United States Patent [19]

Bradbury et al.

[11] Patent Number: 5,885,240
[45] Date of Patent: Mar. 23, 1999

[54] METHOD FOR MEDICAL AND BIOLOGICAL FLUID COLLECTION AND DISPOSAL

[75] Inventors: John R. Bradbury, Strongsville, Ohio; Richard L. Terry, DeSoto; Clayton W. Spangler, Dittmer, both of Mo.

[73] Assignee: Steris Corporation, Mentor, Ohio

[21] Appl. No.: 878,506

[22] Filed: Jun. 18, 1997

Related U.S. Application Data

[62] Division of Ser. No. 398,161, Mar. 2, 1995, Pat. No. 5,741,238.

[51] Int. Cl.⁶ .................................................. A61M 37/00
[52] U.S. Cl. .............................................. 604/4; 210/646
[58] Field of Search ........................... 210/645, 646; 604/317, 259, 260, 319, 320, 321, 322, 4–6

[56] References Cited

U.S. PATENT DOCUMENTS

| | | | |
|---|---|---|---|
| 2,936,757 | 5/1960 | Trace | 128/276 |
| 3,191,600 | 6/1965 | Everett | 128/276 |
| 3,929,133 | 12/1975 | Ragab | 128/277 |
| 4,054,998 | 10/1977 | Hesselgren | 32/33 |
| 4,090,502 | 5/1978 | Tajika | 128/2 A |
| 4,105,031 | 8/1978 | Kurtz et al. | 128/276 |
| 4,135,515 | 1/1979 | Muriot | 128/276 |
| 4,157,718 | 6/1979 | Baehr | 128/276 |
| 4,306,557 | 12/1981 | North | 128/276 |
| 4,333,480 | 6/1982 | Villari et al. | 128/767 |
| 4,464,258 | 8/1984 | Wong et al. | 210/205 |
| 4,493,695 | 1/1985 | Cook | 604/27 |
| 4,505,703 | 3/1985 | Gale et al. | 604/317 |
| 4,540,413 | 9/1985 | Russo | 604/320 |
| 4,626,248 | 12/1986 | Scheller | 604/319 |
| 4,627,833 | 12/1986 | Cook | 604/34 |
| 4,631,050 | 12/1986 | Reed et al. | 604/4 |
| 4,642,093 | 2/1987 | Härle | 604/54 |
| 4,770,787 | 9/1988 | Heath et al. | 210/646 |
| 4,781,707 | 11/1988 | Boehringer et al. | 604/317 |
| 4,808,159 | 2/1989 | Wilson | 604/4 |
| 4,855,064 | 8/1989 | Schlein | 210/764 |
| 4,857,063 | 8/1989 | Glenn | 604/317 |
| 4,863,446 | 9/1989 | Parker | 604/317 |
| 4,867,738 | 9/1989 | Mintz | 604/4 |
| 4,957,491 | 9/1990 | Parker | 604/317 |

(List continued on next page.)

FOREIGN PATENT DOCUMENTS

| | | |
|---|---|---|
| 384 585 | 8/1990 | European Pat. Off. . |
| 390 094 | 10/1990 | European Pat. Off. . |
| WO 93/25248 | 12/1993 | WIPO . |

*Primary Examiner*—John G. Weiss
*Assistant Examiner*—Ki Yong O
*Attorney, Agent, or Firm*—Fay, Sharpe, Beall, Fagan, Minnich & McKee

[57] ABSTRACT

A vessel (20) which is divided into compartments (22, 24) receives medical and biological fluid wastes through inlet fitting (12, 14). As the fluid is received, air in the vessel is displaced and is discharged through a vent line (32), either to atmosphere or to a vacuum source. When a level sensor (34) senses that a level of fluid in the vessel is approaching a preselected maximum, a control circuit (40) closes a valve (30) in the vent line, blocking the discharge of air from the vessel and creating a backpressure that stops the receipt of further fluid. Tubing connected to the fittings (12, 14) is disconnected from the patient or other source of fluid and a valve (64) is manually opened to vent the vessel, allowing any residual fluid in the tubing to be drained into the vessel. A drain valve (74) is opened to drain the vessel and the cleaning cycle is commenced. A fittings bell (194) is placed over each inlet fitting such that water with entrained disinfectant from disinfectant reservoir (122) disinfects the inlet nozzles inside and outside. The water with entrained disinfectant is also circulated through a metering reservoir (144) to spray nozzles (146) which spray down the interior surfaces of the vessel. After the nozzle and vessels have been decontaminated, the drain valve is closed and a valve (148) is opened to empty the metered volume of disinfectant solution from the metering chamber into the vessel.

14 Claims, 3 Drawing Sheets

U.S. PATENT DOCUMENTS

| | | | |
|---|---|---|---|
| 4,976,682 | 12/1990 | Lane et al. | 604/4 |
| 4,986,839 | 1/1991 | Wertz et al. | 55/274 |
| 5,017,135 | 5/1991 | Meyer | 433/92 |
| 5,044,953 | 9/1991 | Sullivan | 433/92 |
| 5,045,077 | 9/1991 | Blake, III | 604/321 |
| 5,047,072 | 9/1991 | Wertz et al. | 55/1 |
| 5,053,025 | 10/1991 | Knippscheer | 604/317 |
| 5,058,619 | 10/1991 | Zheng | 137/240 |
| 5,078,677 | 1/1992 | Gentelia et al. | 604/4 |
| 5,154,712 | 10/1992 | Herweck et al. | 604/321 |
| 5,156,823 | 10/1992 | Hori et al. | 422/292 |
| 5,185,007 | 2/1993 | Middaugh et al. | 604/320 |
| 5,225,158 | 7/1993 | Tayebi et al. | 422/4 |
| 5,238,582 | 8/1993 | Hori et al. | 210/749 |
| 5,242,434 | 9/1993 | Terry | 604/317 |
| 5,277,869 | 1/1994 | Glazer et al. | 422/26 |
| 5,279,600 | 1/1994 | Hogan | 604/317 |
| 5,279,602 | 1/1994 | Middaugh et al. | 604/320 |
| 5,284,621 | 2/1994 | Kaufman | 422/32 |

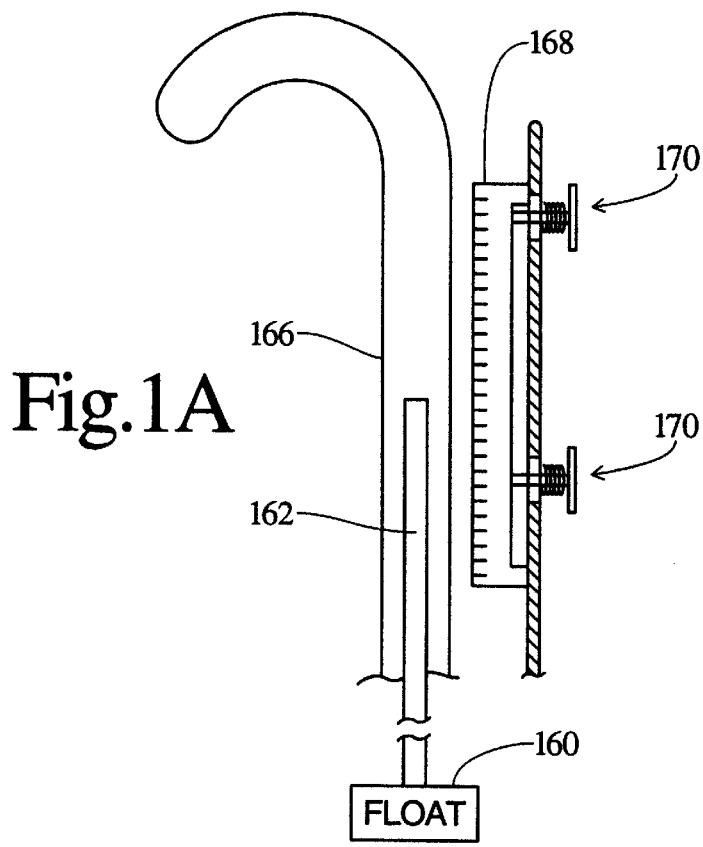
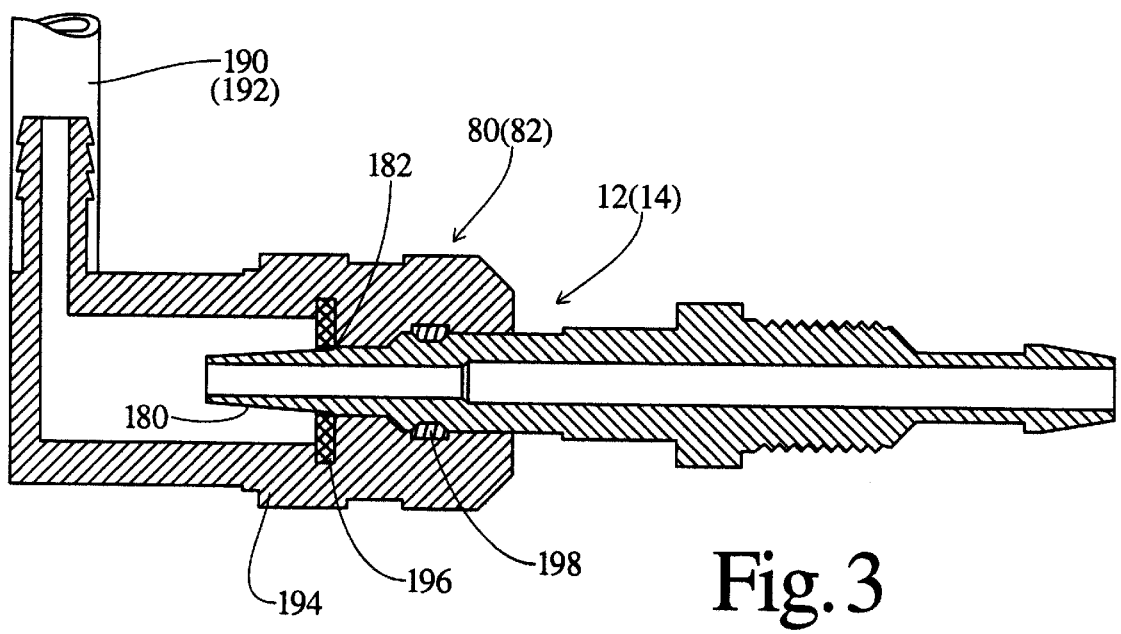

METHOD FOR MEDICAL AND BIOLOGICAL FLUID COLLECTION AND DISPOSAL

This application is a divisional of U.S. application Ser. No. 08/398,161, filed Mar. 2, 1995, now U.S. Pat. No. 5,741,238.

BACKGROUND OF THE INVENTION

The present invention relates to the art of handling biological fluids. It finds particular application in conjunction with the collection, treatment, and disposal of fluid wastes in operating rooms, patient care rooms, emergency care units, and other medical facilities and will be described with particular reference thereto.

Heretofore, various techniques have been used for collecting waste body fluids in conjunction with medical procedures. The collection vessels varied from a simple plastic bag to automated, electrically controlled processing equipment.

The receiving receptacle often varied with the nature and volume of the fluids to be collected. Typical fluids have included blood, urine, mucous, and other body discharges. During some surgical procedures, such as joint surgery, a saline solution or other rinse and lubricating fluid was selectively introduced into the surgical site. The fluid was drawn off from time to time, removing with it surgical scraps, any blood, and other body fluids that may have entered into the surgical site.

Simple bags and pouches could be hung from the surgical table or placed at other convenient locations within the room in which the medical procedure was performed. Flexible tubing typically interconnected the bag with the region of the patient from which the fluid wastes were collected. Such bags or pouches had several drawbacks. First, safe disposal of the fluids was difficult. Such bags or pouches were typically emptied manually, creating the opportunity for direct human contact with potentially infected wastes. Second, difficulties could arise if the volume of drained fluid exceeded the capacity of the bag. Not only would the fluid not drain, but fluid in the bag and the connecting line would be under a positive pressure attributable to the fluid held in the line and resiliency of the bag or pouch. Disconnecting the lines, handling of the pouch, and the like could cause discarded fluids to be reintroduced into the patient or to spurt onto medical personnel, the wound site, or the like.

More elaborate electronically controlled fluid waste removal systems have been utilized, particularly where the fluid waste is removed under suction. Although electronically controlled and of larger capacity, the systems still suffered similar problems. Many required direct manual interaction with medical personnel in order to empty the wastes from the collection reservoir. Others lacked adequate safety features to assure that fluid in the flexible lines would not spurt or be forced back into the patient when the reservoirs become full or during disconnection of the lines. Typically, electronically controlled devices would be dedicated suction or gravity feed devices. In medical procedures in which both gravity and suction drain devices were required, two units would be needed.

Simple collection bags were often discarded as hazardous or potentially hazardous waste, The more complex systems required cleaning and maintenance. Typically, cleaning and maintenance required sufficient human interaction that the human operator was liable to come in contact with a contaminated and potentially infectious surface.

The present invention contemplates a new and improved biological fluid collection, handling, and disposal system which overcomes the above-referenced disadvantages and others.

SUMMARY OF THE INVENTION

In accordance with one aspect of the present invention, an apparatus for handling biological and medical fluid wastes is provided. At least one inlet fitting interconnects with a flexible tube which is connected to a source of fluid waste. A collection vessel is connected with the inlet fitting such that the received fluid waste flows into the vessel. The vessel is selectively drained by a drain line and drain valve. A disinfectant liquid source selectively supplies a disinfectant liquid. A disinfectant fitting which is connected with the source of disinfectant liquid is selectively connectable with the inlet fitting for supplying the disinfectant Liquid through the inlet fitting to the vessel. A vent line and a first valve are connected between the vessel, and either a vacuum source or the atmosphere for removing gases displaced by the collected fluid waste. A level sensor senses a level of fluid waste in the vessel. An automatic shut-off circuit is connected-with the level sensor and the vent valve for selectively blocking the removal of gases from the vessel in response to the level sensor sensing that the fluid waste level in the vessel is approaching capacity.

In accordance with another aspect of the present invention, a manual vent is provided for selectively venting the vessel to atmosphere. The manual vent enables the pressure in the flexible lines to be retrieved prior to disconnection from the vessel even after the electronic control has closed the vent valves.

In accordance with another aspect of the present invention, the level sensor is an analog transducer that is connected to an analog-to-digital converter and a digital readout.

In accordance with another aspect of the present invention, a mechanical float assembly is provided. A float which is interconnected to an indicator rod is disposed in the vessel. A gauge is mounted adjacent the indicator rod for providing a scale for assessing fluid level in the vessel. A mechanical adjustment selectively adjusts the gauge to accommodate an offset in the indicator rod when the vent tube is connected to a vacuum source relative to when the vent tube is connected with the atmosphere.

In accordance with another aspect of the present invention, the vent line is connected with a filter.

In accordance with another aspect of the present invention, a disinfectant concentrate is entrained in a flow of water. A pressure regulator and flow monitor are connected with the received flow of water.

In accordance with another aspect of the present invention, the entrained disinfectant is received from a disinfectant reservoir. A disinfectant supply maintains a level of disinfectant in the reservoir. A monitor provides a signal to the electronic control when the disinfectant concentrate supply fails to maintain the level of disinfectant concentrate in the reservoir.

In accordance with another aspect of the present invention, the liquid disinfectant is pumped through a metering chamber to spray nozzles for flushing an interior of the vessel. After the interior of the vessel has been flushed and the circulation of liquid disinfectant stopped, a valve to the metering chamber is opened, emptying a metered dose of the disinfectant into the vessel for disinfecting subsequently collected fluid wastes.

In accordance with another aspect of the present invention, the inlet fitting has a male portion over which the flexible tube is connected. The disinfectant fitting includes a bell which is spaced from the male portion to provide a liquid circulation region therebetween. In this manner, the disinfectant liquid cleans both the interior and the exterior of the inlet fitting.

One advantage of the present invention is that it is fully automatic. The potential for direct contact between a human patient or operator and the collected fluids is minimized.

Another advantage of the present invention is that it minimizes the potential for fluid in flexible feed lines from spurting onto the patient, attendant, or wound site.

Another advantage of the present invention resides in the automatic decontamination of the apparatus which again minimizes the opportunity for human contact with disposed fluids.

Another advantage of the present invention resides in improved safety, and warning features which inhibit misuse of the equipment.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 1A is a detailed view of the float gauge mounting assembly of FIG. 1;

DETAILED DESCRIPTION OF THE PREFERRED EMBODIMENTS

Figure 1:
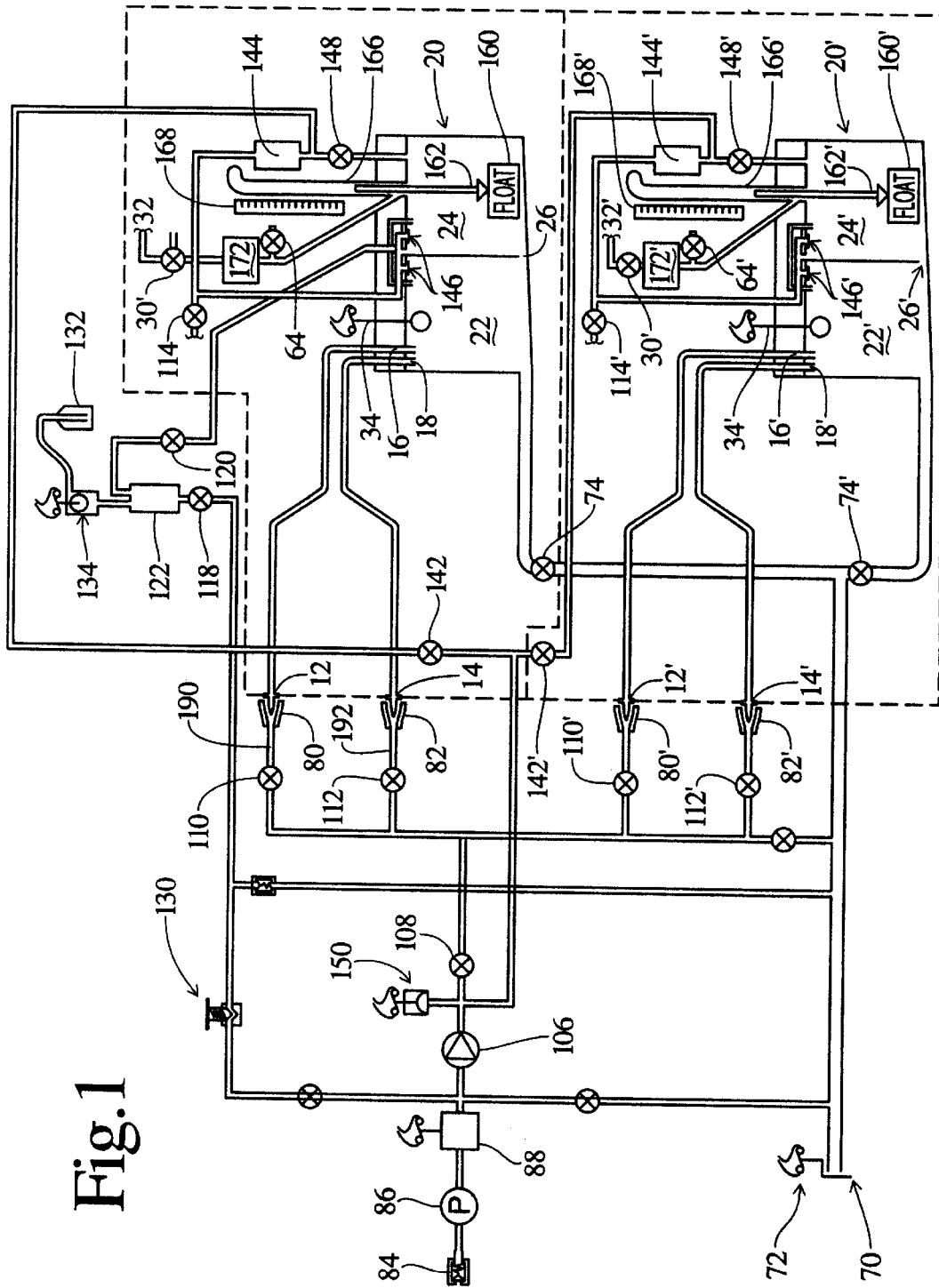
FIG. 1 is a diagrammatic illustration of a biological and medical fluid waste collection, handling, and discharge system in accordance with the present invention.

A common housing holds a first fluid waste receiving assembly 10 and a second fluid waste receiving assembly 10'. Fluid waste receiving assemblies 10 and 10' are significantly analogous that a detailed description will be made to the parts of assembly 10 and the description will be understood as describing the assembly 10' as well. Like parts in assembly 10' are denoted with the same reference numeral as in assembly 10 but followed by a prime (').

A pair of inlet fittings 12, 14 are rigidly mounted to a housing and configured to be received frictionally in flexible tubing which is connected with the patient or other source of fluid waste. The fittings are connected through inlet tubes 16, 18 with a fluid receiving vessel 20. More specifically, the fluid receiving vessel 20 has multiple chambers including a first chamber 22 and a second chamber 24 which are interconnected by a fluid level equalization path 26 adjacent a lowermost end of each. A pressure equalization passage 28 allows the fluid level in the first and second chambers to equalize. The inlet tubes 16, 19 have discharge ends disposed in an uppermost region of the first chamber 22. The fluid discharged from the inlet tubes into the first chamber 22 tends to be turbulent and may have froth or foam on its upper surface. The fluid connection passage 26 allows the least turbulent portion of the fluid at the bottom of the first chamber 22 to flow into the second chamber 24.

When fluid is being received, a valve 30 interconnects a line 32 with the upper region of the second chamber 24. Line 32 is connected to a vacuum if the fluid wastes are to be drawn in under a vacuum or connects with atmosphere if the fluid wastes are to be drained by gravity flow. As the fluid level within the clambers rises, a level sensor such as a float switch 34 senses the level of the fluid in the vessel 20. The level sensor 34 sends signals to an electronic control circuitry 40 indicative of the level of fluids in the vessel 20. Before the level of the fluid reaches the lowermost surface of the inlet tube 16, 18, the collection of fluid wastes is terminated.

Figure 2:
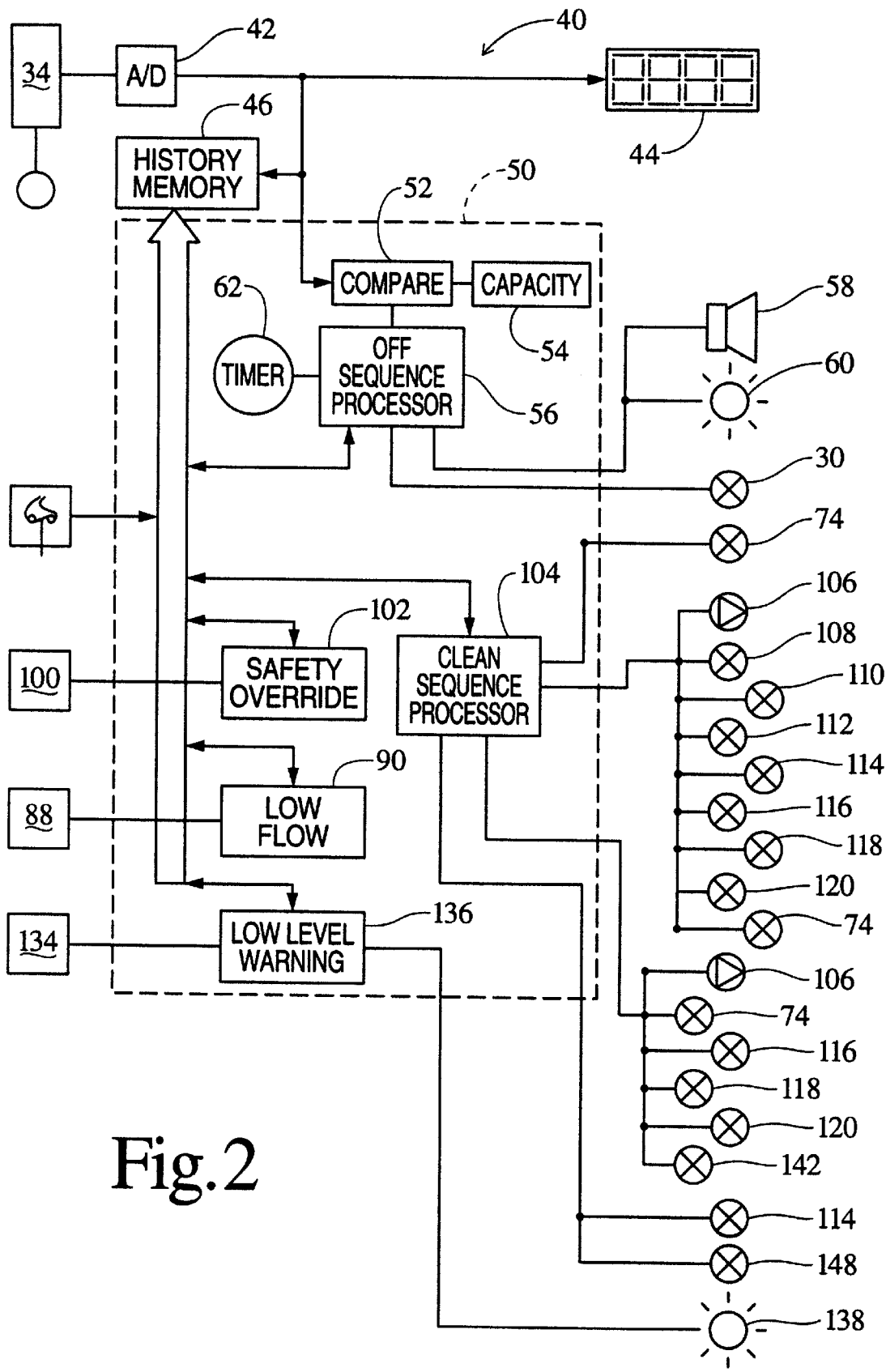
FIG. 2 is a diagrammatic illustration of an electronic control circuit in accordance with the present invention for the system of FIG. 1; and, FIG. 3 is a detailed view of partial section of a self-sterilizing fluid coupling assembly in accordance with the present invention.

With continuing reference to FIG. 1 and further reference to FIG. 2, an electronic control 40, among other operations, terminates venting/suction when the vessel 20 becomes filled. More specifically the output of the level sensor 34 is conveyed to an analog-to-digital converter 42 which digitizes the level signal. A digital display 44 provides the operator with a digital display of capacity remaining. Alternately, the digital display 44 can provide an indication of the volume of fluid collected. The received fluid and level information is stored in a history memory 46.

A microprocessor controller 50 includes a comparator 52 which compares the digital fluid level signal with a capacity from a capacity memory 54. When the full capacity is reached the comparator starts an off or termination sequence processor 56. Initially upon reaching capacity, the off sequence processor 56 actuates an audio alarm 58 and a visual alarm 60. A predetermined time later, e.g., 30 seconds, as determined by a timer 62, or a predetermined fluid level increase later as determined from the digital level signal from the level sensor 34, the off sequence processor closes valve 30. If the system is connected with a vacuum source, this terminates the draw of the vacuum source. If connected to atmosphere for gravity drain, this closes the atmospheric vent to create backpressure terminating the ingress of fluid wastes. The off sequence processor communicates the level, time, and other termination sequence information to the history memory 46. A manually operated valve 64 is selectively operated by the attendant after the inlet ends of the flexible tubing have been disconnected from the source of the fluid waste. Opening valve 64 again vents the vessel 20 to atmosphere, allowing any residual pressure in the lines and the inlet tubes 16, 18 to be safely relieved to atmosphere. The inlet fittings 22 and 12, are physically positioned at a higher elevation than the top of the vessel 20 such that gravity causes any remaining fluids therein to flow into the vessel 20.

When the tubes are disconnected from the collection system 10, they may be reconnected immediately to collection system 10' for the collection of further fluids, unless system 10' is already connected to other sources of fluid waste is at capacity.

In a portable embodiment, the collection systems 10, 10' are housed in a common wheeled housing After the vessels are filled, the housing is wheeled to a drain into which the fluids in the vessels 20 and 20' are drained. For most biological fluids the drain can be a standard sanitary or sewer drain The waste biological fluids present a biological load to the sewage treatment station which is analogous to the load traditionally sent into sewage treatment stations. Once an outlet is positioned adjacent or in the receiving drain, an attendant connects a drain hose outlet 70 to a drain hose which direct effluent to a drain. A drain hose sensor switch 72 checks the presence of the drain hose to assure that a drain valve 74 will not be opened in its absence. The attendant further connects fittings 80, 82 with the inlet fittings 12, 14. The fittings 80, 82 are connected to flexible fluid supply tubing lengths which extend out of the housing. In the portable unit, a water inlet fitting 84 is interconnected with a source of water. In the built-in embodiment, the system is connected directly with the plumbing system of the building. During a clean cycle, a pressure regulator 86 limits the pressure of the incoming water. A flow monitor 88 monitors the flow rate of the received water. The flow monitor 88 produces a digital output signal indicative of the flow rate which output signal is conveyed to the history memory 46 and to a low flow rate warning circuit 90. The flow rate warning circuit compares the flow rate with an appropriate flow rate for the current cycle as supplied by the history memory 46. When an insufficient fluid flow rate is provided, the flow rate sensor triggers an alarm 92 to alert the attendant that there is insufficient water flow for proper operation.

In a stationary embodiment, the housing is mounted to a wall in the medical facility and the outlet is permanently connected with sanitary plumbing of the building. In the stationary embodiment, a drain outlet 70 and a drain hose sensor switch 72 are not strictly necessary for operation but are preferably still retained for such times as when maintenance dictates removal of the entire assembly from the Shall mounting In the stationary embodiment, the off sequence processor 56 automatically opens the drain valve 74 when the level sensor 34 senses that the fluid level in the vessel 20 is at or is approaching capacity.

The operator depresses a button 100 to initiate draining of the vessel 20 and begin the clean cycle. When this occurs, a safety override circuit 102 queries the history memory 46 to determine whether the system is in an appropriate state to be drained. It the history memory 46 is in the appropriate state to be drained, then the safety override allows a drain-valve 74 to be opened. For safety, the drain hose presence switch 76 detects that a drain hose has been connected to the unit. That information is communicated to the history memory 46. If the drain hose is not connected, the safety override 102 will prevent the valve 74 from opening. Analogously, if the drain hose 76 is connected, the safety override 102 will allow the drain valve 74 to open and vessel 20 drains.

Upon completion of draining the vessel 20, and if everything is in the appropriate state for the cleaning cycle, a cleaning sequence processor 104 actuates a pump 106, opens a fluid inlet valve 108, and opens fluid inlet valves 110, 112 concurrently or sequentially. Depending on water pressure and flow rates, fittings 12 and 14 may be cleaned concurrently or sequentially. Analogously, vessels 20 and 20' may be cleaned either concurrently or sequentially. While the water is flowing through the inlet fittings 12 and 14, the cleaning sequence processor maintains the drain valve 74 in an open state so that the rinse water can drain and opens a valve 114 or the valve 30 to vent the vessel to atmosphere.

In order to disinfect the inlets 12, 14 and other portions of the system, a back flush check/solenoid valve 116, a disinfectant supply valve 118, and a disinfectant supply vent valve 120 are opened. This enables a disinfectant to be drawn from a reservoir 122 and entrained into the incoming water received by the pump 106.

The disinfectant supply system includes a metering valve 130 which regulates the volume of disinfectant provided. The disinfectant chamber 122, in the preferred embodiment, holds a sufficient volume of disinfectant for a disinfection cycle. A disinfectant source or supply 132 provides additional disinfectant to the chamber 122 as it is used. A disinfectant level sensor 134 monitors the level of disinfectant in the chamber 122. In particular, when the disinfectant source 132 runs dry and can no longer maintain the disinfectant chamber 122 full, the level sensor 134 conveys this information to the history memory 46 and causes a low disinfectant level warning circuit 136 to actuate a low disinfectant alarm 138. If the low disinfectant level is not corrected and the correction information conveyed to the history memory 46 by the low disinfectant sensor 134, the safety override circuit 102 prevents further cleaning cycles from being initiated.

After the inlet fittings 12, 14 and associated tubing have been flushed and disinfected for a preselected duration as timed by a timer 140, the cleaning sequence processor 104 closes valves 108, 110, 112, and 114, and opens valve 142. The disinfectant supply valves 116, 118, and the vent valve 120 remain held open, as does the drain valve 74. In this state, continued operation of pump 106 pumps the disinfecting solution through a metering chamber 144 and through a pair of spray nozzles 146. The spray nozzles are configured to spray down the interior surfaces of the first chamber 22 and the second chamber 24 of the waste collection vessel 20. In one embodiment, the spraying is relied upon to disinfect the interior surfaces of the waste collection vessels In an alternate embodiment, the valve 74 is closed after a preselected spraying duration and the first and second chambers 22 and 24 are allowed to fill. When the level sensor valve 34 senses that the first and second chambers have been fully filled, operation of the pump 106 is terminated and the solution is allowed to sit for a preselected disinfecting duration. Thereafter, the drain valve 74 is opened allowing the first and second chambers to drain. Preferably, the pump 106 is restarted to spray down the inside of first and second chambers during draining.

In the next stage, the disinfectant supply valves 116, 118, 120 are closed, pump 106 is stopped, and valve 142 is closed. The drain valve 74 is also closed, but preferably with a sufficient delay to allow residual liquids to drain fully after pumping of disinfectant fluid has stopped. After the drain valve 74 has closed, the vent valve 114 and a valve 148 are opened, allowing the disinfectant solution trapped in the metering chamber 144 to be drained into the first and second chambers 22, 24. In this manner, a dose of disinfectant is charged into the vessel 20 prior to biological fluid collection. After the disinfectant solution has been charged into the collection vessel, the valves 114 and 148 are closed and another fluid collection cycle can be commenced.

A pressure switch 150 is connected adjacent an output end of the pump 106 and with the memory history 46. An overpressure sensor 152 compares the pressure from the pressure sensor 150 with acceptable operating pressures for the pump. In an overpressure situation, the pressure indicator switch through the memory history and the safety overrides terminates operation of the pump and alerts the attendant of a malfunction.

With reference to FIG. 1A, in addition to the digital readout 44, a mechanical indicator of fluid level in the vessel 20 is provided. More specifically, a float 160 is interconnected with a float rod 162. The float rod 162 extends through an at least partially transparent sealed tube 166 at the top of the vessel 20. The level of the float rod 162 in the tube 166 is indicative of the level to which the vessel 20 is filled. A gauge 168 is mounted behind the tube 166. In order to permit easy calibration of the gauge 168, the gauge is adjustably mounted. In the illustrated embodiment, the gauge includes two pair of spring clamps 170 which holds the gauge in position relative to the tube 166. Optionally, a screw clamp may be provided to lock the gauge more securely in the selected position. Various other structures for adjusting and recalibrating the gauge 168 are contemplated. Because recalibration is most commonly needed when changing between a vacuum source or gravity feed, there are two primary calibration positions. Stops, interchangeable gauge markers, and the like may be provided for shifting the gauge quickly between vacuum and gravity feed positions.

The vacuum/atmosphere connection line 32 is interconnected with a filter 172. The filter is preferably a hydrophobic microporous filter with sufficiently small pore size that bacteria and microbes and aerosols will riot pass therethrough. In this manner, any potentially harmful microbes are trapped against exiting into the ambient atmosphere.

With reference to FIG. 3, each of the fittings 12, 14, include a male portion 180 over which the length of flexible hose is received. A stop 182 limits receipt of the flexible hose. Some of the biological fluid waste may seep between the flexible tube and the male portion, leaving a residue of potentially contaminated fluids on the male portion of the fitting. The female decontamination fitting 80, (82) is connected by a flexible hose 190, (192) with the valve 110, 112. During the cleaning step, the female fitting is inserted over the male fitting and the stop, forming a fluid tight seal with the stop. The female fitting includes an outer flange or bell portion 194. A fluid passage is defined between the male portion, the stop surface, and the bell such that the disinfectant fluid flows therebetween. A seal 196 retains the disinfectant solution within the chamber defined by the bell. A lock or latching mechanism 198, such as a snap ring, latches the bell 194 to the male fitting to assure a tight, secure interconnection.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of handling medical and biological fluid waste comprising:

receiving the fluid waste through a fluid line connected to a source of the fluid waste through an inlet fitting, collecting the fluid waste in a vessel, and discharging gases and vapors displaced from the vessel through a vent passage;

monitoring a level of the fluid waste in the vessel;

in response to the monitored fluid level reaching a preselected level, providing a warning to an attendant and closing the vent passages to prevent the discharge of gases and vapors, the closing the vent passage creating a back pressure in the vessel which inhibits the receipt of further fluid waste;

disconnecting the fluid line from the source of the fluid waste;

manually venting the vessel to reduce the back pressure until residual fluid waste in the fluid line has drained into the vessel; and draining the vessel.

2. The method as set forth in claim 1 further including connecting the vent passage to a vacuum source.

3. The method as set forth in claim 1 further including discharging the vent passage through a filter to ambient atmosphere.

4. A method of handling medical and biological fluid waste comprising:

receiving the fluid waste through a fluid line connected to a source of the fluid waste through an inlet fitting, collecting the fluid waste in a vessel, and fitting, collecting the fluid waste in a vessel, and discharging displaced gases and vapors through a vent line;

monitoring a level of the fluid waste in the vessel;

in response to the monitored fluid level reading a preselected level, stopping the vessel from receiving further fluid waste;

draining the vessel;

disconnecting the fluid line from the inlet fitting;

circulating a disinfectant fluid around and through the inlet fitting and into the vessel; and draining the disinfectant fluid from the vessel at least partially.

5. A method of handling medical and biological fluid waste comprising:

receiving the fluid waste from a fluid line connected to a source of the fluid waste through an inlet fitting and collecting the fluid waste in a vessel, as the fluid waste is collected in the vessel, discharging displaced gases and vapors through a vent line;

monitoring a level of the fluid waste in the vessel;

in response to the monitored fluid level reaching a preselected level, terminating the receipt of further fluid waste in the vessel;

disconnecting the fluid line from the source of the fluid waste;

manually venting the vessel until residual fluid waste in the fluid line has drained into the vessel; and draining the vessel;

circulating a disinfectant fluid to at least one spray nozzle disposed adjacent an upper surface of the vessel;

with disinfectant fluid discharged from the spray nozzle, rinsing interior surfaces of the vessel; and, draining the disinfectant fluid from the vessel.

6. The method as set forth in claim 5 further including:

circulating the disinfectant fluid into a metering chamber, out an upper end of the metering chamber, and to the spray nozzles;

terminating the circulating of the disinfectant fluid such that a metered volume of the disinfectant fluid is held in the metering chamber;

draining the vessel;

closing a vessel drain;

emptying the metering chamber into the vessel such that a metered dose of decontaminant fluid is charged into the vessel;

collecting fluid waste in the vessel such that the metered volume of decontaminant fluid assist in decontaminating the received fluid waste.

7. The method as set forth in claim 4 wherein supplying the disinfectant fluid includes entraining a metered amount of disinfectant concentrate in water under pressure.

8. The method as set forth in claim 7 further including entraining the disinfectant concentrate from a disinfectant concentrate reservoir;

maintaining the disinfectant concentrate in the reservoir at a preselected level with the disinfectant concentrate from a disinfectant source;

monitoring at least one of the disinfectant concentrate level in the reservoir and the resupply of disinfectant concentrate from the disinfectant source and providing a warning when the disinfectant concentrate reservoir falls below a preselected level.

9. A method of handling medical and biological fluid waste comprising:

receiving the fluid waste from a fluid line connected to a source of the fluid waste through an inlet fitting and collecting the fluid waste in a vessel, as the fluid waste is collected in the vessel, discharging displaced gases and vapors through a vent passage;

monitoring a level of the fluid waste in the vessel;

in response to the monitored fluid level reaching a preselected level, providing a warning to an attendant to close the vent passage to create back pressure in the vessel which inhibits the receipt of further fluid waste;

disconnecting the fluid line from the inlet fitting;

placing a bell over the inlet fitting such that an open circulation region is defined between the bell and the inlet fitting;

circulating a disinfectant fluid through the circulation region and through the inlet fitting.

10. A method of handling medical and biological fluid waste comprising:

receiving the fluid waste from a fluid line connected to a source of the fluid waste through an inlet fitting and collecting the fluid waste in a vessel, as the fluid waste is collected in the vessel, discharging displaced gases and vapors through a vent line;

monitoring a level of the fluid waste in the vessel;

in response to the monitored fluid level reaching a preselected level, providing a warning to an attendant to terminate the receipt of further fluid waste;

draining the waste fluid from the vessel;

flushing interior surfaces of the vessel with a disinfectant fluid to flush a residue of the fluid waste from the vessel interior surfaces;

at least partially draining the disinfectant fluid from the vessel.

11. The method as set forth in claim 10 further including:

supplying the disinfectant fluid from a reservoir;

monitoring a level of the disinfectant fluid in the reservoir;

signalling a low level of the disinfectant fluid.

12. A method for biological fluid waste collection and disposal, the method comprising:

passing fluid waste through a flexible tube and through a first connector of an inlet fitting of a biological handling and disposal apparatus including:

a collection vessel connected with the inlet fitting for receiving the fluid waste;

a drain line and a drain valve connected with the vessel for draining the vessel;

a bell fitting connected with a source of disinfectant liquid and connectable with a second connector disposed adjacent to the first connector, with the first connector received in and displaced from the bell fitting, such that a fluid circulation region is defined between the bell fitting and the first connector;

a vent line connected between the vessel and one of (1) a vacuum source and (2) the atmosphere for removing gases displaced by collected fluid waste from the vessel;

a level sensor for sensing a level of fluid waste in the vessel;

opening the drain valve and draining the fluid from the vessel through the drain line;

disconnecting the flexible tube from the first connector;

connecting the bell fitting with the second connector;

passing the disinfectant liquid from the source of the disinfectant liquid through the bell fitting, around and through the first connector to the vessel.

13. The method as set forth in claim 12 further including:

selectively closing a vent valve in the vent line to stop the fluid waste from passing through the inlet fitting into the vessel.

14. The method as set forth in claim 12 further including:

after draining the disinfectant liquid from the vessel, maintaining a small volume of disinfectant liquid in the vessel to disinfect fluid waste entering the vessel.

* * * * *